(12) United States Patent
Neilan et al.

(10) Patent No.: US 10,980,923 B2
(45) Date of Patent: Apr. 20, 2021

(54) IMPLANTABLE MEDICAL DEVICE WITH DIFFERENTIATED LUMINAL AND ABLUMINAL CHARACTERISTICS

(71) Applicant: Cook Medical Technologies LLC, Bloomington, IN (US)

(72) Inventors: John Neilan, Gort (IE); David Murray, Limerick (IE); James Butler, Aherlow (IE)

(73) Assignee: Cook Medical Technologies LLC, Bloomington, IN (US)

( * ) Notice: Subject to any disclaimer, the term of this patent is extended or adjusted under 35 U.S.C. 154(b) by 324 days.

(21) Appl. No.: 15/932,323

(22) Filed: Feb. 16, 2018

(65) Prior Publication Data
US 2018/0228944 A1    Aug. 16, 2018

Related U.S. Application Data

(60) Provisional application No. 62/459,844, filed on Feb. 16, 2017.

(30) Foreign Application Priority Data

Feb. 16, 2017   (GB) ..................................... 1702525

(51) Int. Cl.
| | |
|---|---|
| A61L 31/00 | (2006.01) |
| A61L 31/16 | (2006.01) |
| A61L 31/02 | (2006.01) |
| A61L 31/08 | (2006.01) |
| A61L 31/14 | (2006.01) |
| A61L 27/08 | (2006.01) |
| A61L 27/54 | (2006.01) |

(52) U.S. Cl.
CPC ............. *A61L 31/16* (2013.01); *A61L 31/022* (2013.01); *A61L 31/024* (2013.01); *A61L 31/084* (2013.01); *A61L 31/14* (2013.01); *A61L 27/08* (2013.01); *A61L 27/54* (2013.01); *A61L 2400/18* (2013.01); *A61L 2420/02* (2013.01)

(58) Field of Classification Search
None
See application file for complete search history.

(56) References Cited

U.S. PATENT DOCUMENTS

| | | | |
|---|---|---|---|
| 4,718,907 A | 1/1988 | Karwoski et al. | |
| 5,289,831 A | 3/1994 | Bosley | |
| 6,090,134 A | 7/2000 | Tu et al. | |
| 7,770,536 B2 | 8/2010 | Chen et al. | |
| 8,353,949 B2 | 1/2013 | Weber et al. | |
| 8,523,937 B2 | 9/2013 | Lindsay et al. | |
| 2003/0113478 A1 | 6/2003 | Dang et al. | |
| 2005/0238684 A1* | 10/2005 | Helmus .................. | A61L 27/34 424/423 |
| 2008/0008654 A1* | 1/2008 | Clarke .................. | A61L 27/306 424/9.4 |
| 2008/0166470 A1* | 7/2008 | Schwartz ............... | B05D 1/185 427/2.27 |
| 2010/0215643 A1 | 8/2010 | Clevenger et al. | |
| 2016/0361472 A1* | 12/2016 | Neilan .................... | A61L 31/16 |

FOREIGN PATENT DOCUMENTS

| | | |
|---|---|---|
| EP | 0850604 A2 | 7/1998 |
| EP | 0850604 B1 | 7/1998 |
| EP | 18275023.2 | 7/2018 |
| GB | 1702525.5 | 8/2017 |
| WO | 00-10622 A1 | 3/2000 |
| WO | WO 00-10622 A1 | 3/2000 |
| WO | 2008002778 A2 | 1/2008 |
| WO | WO 2008-002778 A2 | 1/2008 |
| WO | 2013152713 A1 | 10/2013 |
| WO | WO 2013-152713 A1 | 10/2013 |

OTHER PUBLICATIONS

GB Search & Exam Report, Appl. No. GB1702525.5, Cook Medical Technologies LLC, dated Aug. 15, 2017.
EP 18275023.2 EU Search Report, Cook Medical Technologies LLC, dated Jul. 16, 2018.

* cited by examiner

*Primary Examiner* — Susan T Tran
(74) *Attorney, Agent, or Firm* — Woodard, Emhardt, Henry, Reeves & Wagner, LLP

(57) ABSTRACT

There are disclosed implantable medical devices and apparatus for treating implantable medical devices during production, so as to cause the implantable medical devices to have abluminal surfaces and luminal surfaces with different functional characteristics and in particular surface energies. The luminal surfaces of the medical device are preferably coated with carbon, so as to have a low surface energy, which reduces the risk of thrombi forming when implanted into a patient's vessels. The abluminal surfaces are treated so as to have a high surface energy, such that a therapeutic, preferably bioactive, material, such as a drug, can adhere to the abluminal surfaces and preferably without any need for a containment layer such as polymer or other matrix material. Once the therapeutic material has been delivered into the tissue wall, the stent can remain within the patient's vessel without leaving any delivery artefacts, as occurs with some prior art drug eluting medical devices.

18 Claims, 7 Drawing Sheets

IMPLANTABLE MEDICAL DEVICE WITH DIFFERENTIATED LUMINAL AND ABLUMINAL CHARACTERISTICS

CROSS REFERENCE TO RELATED APPLICATIONS

This application claims the benefit of Great Britain patent application No. 1702525.5 filed on Feb. 16, 2017 and U.S. provisional patent application No. 62/459,844 filed on Feb. 16, 2017, entitled "Implantable Medical Device with Differentiated Luminal and Abluminal Characteristics" the entire contents of which are incorporated herein by reference.

TECHNICAL FIELD

The present invention relates to an implantable medical device such as a stent, stent graft, vascular filter or plug, valvuloplasty device and so on. The medical device is preferably at least partially coated with a bioactive agent, in the preferred embodiments on its abluminal surfaces.

BACKGROUND OF THE INVENTION

Coated medical devices, particularly endoluminally deployable medical devices, are known for a variety of medical applications. In the case of an implantable medical device, that is a device intended to be left in the patient permanently or over long periods of time, the device may coated with one or more layers of drug intended for long term drug administration to diseased tissue. Treatment of cancers is an example. In other examples, the coating is provided in order to treat adverse body reactions caused by the medical treatment or by long term presence of a foreign object in the body, such as initial reactive hyperplasia, restenosis and so on.

It is known to provide on a medical device a polymer or other layer which acts as a containment matrix to hold the bioactive agent to the medical device and to control the release of the agent over time. Drug dosing (the amount of drug that is applied to the medical device) and drug adherence (the quantity of drug that sticks/bonds to the surface of the medical device and the quality of bonding) are critical parameters that need to meet strict criteria set by the FDA USP pharmacopeia drug delivery regulations, as well as of other regulatory authorities. The use of polymers layers, or other containment layers, can provide adequate dosing and drug adherence and for this it is known to use both biodegradable and non-biodegradable polymers. Examples of biodegradable polymers include polyglycolic acid/polylactic acid, polycaprolactone, polyhydroxybutarate valerate, polyorthoester and polyenthylenoxide/polybutylene terephthalate. Examples of non-biodegradable polymers include polyurethane, silicone and polyethylene terephthalate.

Such polymer and other layers, however, can cause complications including, for instance, inflammation and exaggerated neointimal proliferative response. In addition, some polymer coatings can provoke an enhanced thrombotic response.

Challenges therefore remain as to how best to apply a bioactive agent, such as a drug, to an implantable medical device while addressing the issues of side effects caused by the bioactive agent carrier or containment device and the issue of risk of thrombosis caused by the implanted device.

In addition to addressing side effects which can be exhibited with drug carriers, it is important to reduce the risk of thrombus formation caused by the implanted the medical device, which can lead to narrowing or closure of the vessel by clotting.

Some examples of surface treated stents are disclosed in U.S. Pat. Nos. 6,090,134, 7,770,536, 4,718,907, 8,523,937, 8,353,949 and US-2010/0215643, as well as in "Plasma-synthesised carbon-based coatings for cardiovascular applications" by M Santos et al in ScienceDirect, Biosurface and Biotribology, vol. 1 (2015) pp 146-160.

SUMMARY OF THE INVENTION

The present invention seeks to provide an improved implantable medical device and method of preparing such a device.

In particular, the teachings herein are aimed at creating different surface characteristics on the luminal and abluminal surfaces of an implantable medical device in order to address the different issues associated with the implantation of such devices both short term and long term in a patient. In the preferred embodiments the device has abluminal surfaces which are optimised for carrying a therapeutic agent such as a bioactive agent, and luminal surfaces which are intended to minimise thrombosis, in particular while avoiding the need for any containment or other matrix layer on the surfaces of the medical device. In the preferred embodiments, the medical device is treated to exhibit different surface energies on its abluminal and luminal surfaces.

According to an aspect of the present invention, there is provided an implantable medical device including a support structure having at least one abluminal surface having a first surface energy, and at least one luminal surface having a second surface energy, the second surface energy being less than the first surface energy; wherein the at least one luminal surface includes a coating of or comprising carbon.

Preferably, the medical device includes a therapeutic material, such as a bioactive material, disposed on the at least one abluminal surface.

The medical device is provided with differentiated abluminal and luminal surfaces to its support structure, such that they provide different functional characteristics. In the preferred embodiment, the at least one abluminal surface has a surface energy sufficient to hold therapeutic agents, such as bioactive agents, such as drugs, thereto without the need for a containment or time release element such as a polymer or other matrix. The at least one luminal surface preferably has a much lower surface energy and such as to exhibit significantly reduced adhesion characteristics, useful in reducing the risk of thrombus formation at the luminal surface or surfaces of the structure.

As will be apparent from the embodiments described below, the at least one luminal surface forms the interior surface of the medical device and therefore the surface or surfaces which are exposed to blood flow. By contrast, the abluminal surface or surfaces typically abut the vessel wall.

The ability to avoid use of other materials or elements to hold the therapeutic and optionally bioactive material to the support structure avoids the foreign body reactions which can be experienced in clinical use with devices which use containment or time release materials.

Preferably, the coating of carbon on the at least one luminal surface is an innermost surface of the medical device. The coating of carbon can provide a substantially reduced surface energy.

In the preferred embodiments the at least one abluminal surface is a functionalised surface. Functionalisation as used herein denotes the treatment of the or one or more surfaces of the medical device to cause a change in the surface characteristics of the structure or a part of the structure.

The at least one luminal surface of the support structure advantageously includes an oxide layer, the coating of carbon being disposed over the oxide layer.

The at least one abluminal surface is free of polymer and matrix materials and preferably free of containment and time release elements.

In the preferred embodiments the device includes a therapeutic material coating, optionally a bioactive material coating, disposed directly on the at least one abluminal surface so as to overlie the at least one abluminal surface, the therapeutic, optionally bioactive, material coating attaching to the at least one abluminal surface as a result of the first surface energy thereof.

The abluminal surface or surfaces may be functionalised by at least one polar acid or polar base component, so as to be a functionalised surface. In these embodiments, a therapeutic material coating, optionally a bioactive material coating, may be disposed directly on the at least one abluminal surface so as to overlie the at least one abluminal surface, the coating being a conjugate base or including a conjugate base component of the polar acid or being a conjugate acid or including a conjugate acid component of the polar base.

Advantageously, the or a therapeutic, optionally bioactive, material coating disposed directly on the at least one abluminal surface so as to overlie the at least one abluminal surface is free of containment or time release materials.

The device may be a stent, typically of substantially tubular form.

The abluminal surface is advantageously a therapeutic material carrying surface, optionally a bioactive material carrying surface.

In some embodiments the at least one abluminal surface is coated with a layer of paclitaxel. Other therapeutic and optionally bioactive agents may be applied to the medical device, in addition to or instead of paclitaxel. Examples are given in the specific description which follows.

According to another aspect of the present invention, there is provided a method of preparing an implantable medical device as specified herein, including the steps of:

treating the at least one abluminal surface of the support structure to increase the surface energy of the at least one abluminal surface relative to the at least one luminal surface, said treatment step not being carried out on the at least one luminal surface.

Preferably, the abluminal surface is treated by functionalisation. This may be by at least one polar acid or by at least one polar base component. The method may include the steps of subjecting the at least one abluminal surface to a treatment or functionalisation agent while keeping the at least one luminal surface apart from the treatment or functionalisation agent. For this purpose, the at least one luminal surface may be covered during treatment or functionalisation of the at least one abluminal surface.

In one embodiment, the at least one abluminal surface is passed through a bath of functionalising solution while the at least one luminal surface is kept away from the functionalising solution.

The method may include the step of washing the entire support structure in an alcohol, sealing the at least one luminal surface and plasma cleaning the at least one abluminal surface. The alcohol is preferably ethanol.

The at least one luminal surface can be sealed by disposing the support structure on a mandrel, wherein the mandrel covers the at least one luminal surface.

Advantageously, the method includes the step of depositing an acid or base functionalisation component to the at least one abluminal surface. The depositing step may be by one of: vapour deposition, spraying, dipping or rolling.

At least the abluminal surface or surfaces are advantageously plasma cleaned. In some embodiments, both the abluminal and luminal surfaces are plasma cleaned.

In other embodiments, at least the abluminal surface or surfaces are cleaned by UV Ozone.

The method may include the step of applying a carbon deposit over at least the luminal surface or surfaces. Carbon deposits may be applied by exposing to air or by a carbon deposition step.

Other aspects and advantages of the teachings herein are described below in connection with the preferred embodiments disclosed herein.

BRIEF DESCRIPTION OF THE DRAWING

Embodiments of the present invention are described below, by way of example only, with reference to the accompanying drawings, in which.

DETAILED DESCRIPTION

Figure 1:
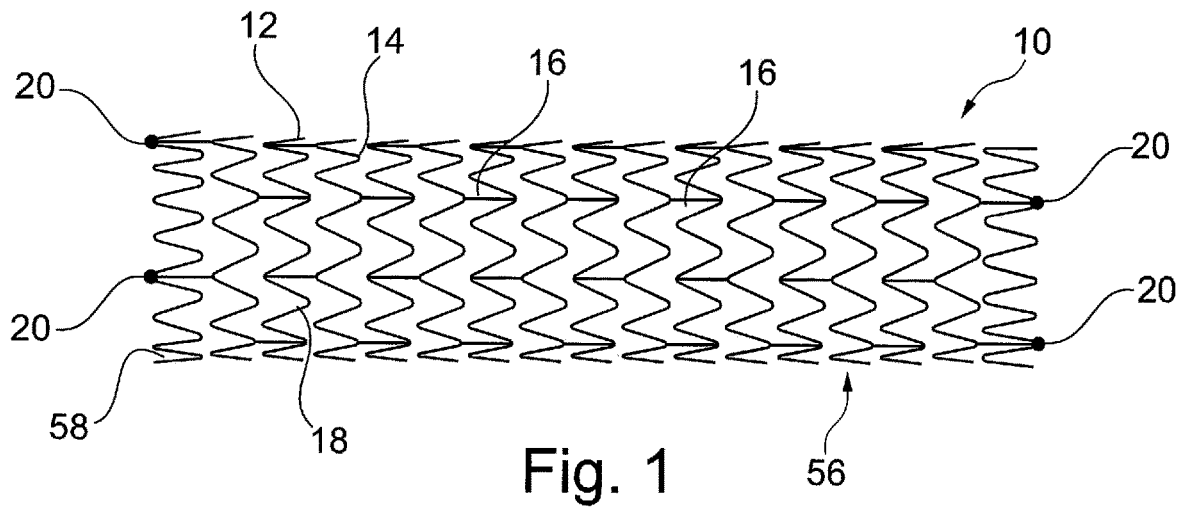
FIG. 1 is a side elevational view of an exemplary vascular stent.

It is to be understood that the drawings are schematic only and not to scale. Often, only the principal components relevant to the teachings herein are shown in the drawings, for the sake of clarity.

The embodiments described below focus on a coated stent. It is to be understood, however, that these are examples only and that the teachings herein can be applied to a large range of medical devices, both for temporary placement in a patient and also for long term placement. Other examples include stent grafts, vascular filters and plugs, and so on.

Referring first to FIG. 1, there is shown an exemplary vascular stent 10 to which the teachings herein can be applied. The stent 10 is generally a tubular structure 12, in this example formed of a plurality of stent rings 14 which extend in series coaxially along the length of the tubular structure 12 and which are coupled to one another by means of tie bars 16, well known in the art. In this example, the stent rings 14 are formed of a plurality of strut sections 18 arranged a zigzag shape. At the end of the stent 10 there may be provided radiopaque markers 20, again of a type well known in the art.

The stent 10 may be self-expanding or balloon expandable and made of any suitable material, of which many are known in the art.

Figure 2:
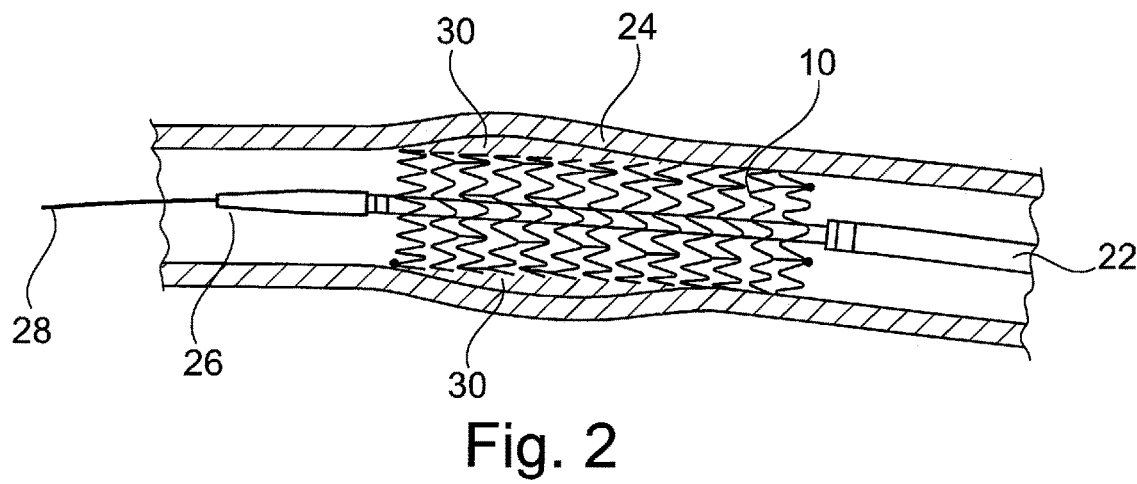
FIG. 2 is a schematic representation of the stent of FIG. 1 in the process of being deployed in a patient's vessel to treat a stenosis.

Referring also to FIG. 2, the stent 10 can be seen in the process of being deployed into a vessel 24, by means of an introducer assembly of which the distal end components 22 are visible in the Figure. These typically include a carrier element having a dilator tip 26 at the distal end thereof. The dilator tip 26 has a lumen therein for the passage of a guide wire 28. The components of the introducer assembly are not relevant to the teachings herein.

In the example in FIG. 2, the stent 10 is being deployed in order to treat a stenosis 30 of the vessel 24 and also to keep the vessel 24 open for the passage of blood therethrough.

Often, the deployment of a stent alone in the vessel does not provide a permanent solution as restenosis can often occur, closing the vessel again. This can be caused by a number of factors, including damage to the tissue of the vessel 24 during the vessel opening or angioplasty procedure, reoccurrence of the original causes of the stenosis, body reaction to the presence of a foreign body in the vessel, and so on.

It has been found that the administration of suitable bioactive agents into the vessel wall from the stent and/or from a medical delivery balloon can substantially retard or prevent subsequent closure of the vessel due to restenosis. A variety of bioactive agents suitable for such purposes are known in the art including, for instance, anti-thrombogenic agents, thrombin inhibitors, tissue plasminogen activators, thrombolytic agents, fibrinolytic agents, vasospasm inhibitors, antiplatelet agents, anti-proliferative agents and so on. A particularly effective bioactive agent known in the art is paclitaxel, others including dexamethasone, heparin and numerous other agents and compounds. A list of suitable bioactive agents is given at the end of this specification, though it is to be understood that the list is not exhaustive.

In addition to or as an alternative to bioactive agents, it can be advantageous to include other therapeutic agents which are not necessarily bioactive. Examples of suitable therapeutic materials are provided towards the end of this description.

Embodiments of the invention include a therapeutic material disposed on the medical device, which in some embodiments is bioactive. The majority of the description below discusses a bioactive material, but this is by way of example only and other embodiments may include a therapeutic material which is not bioactive.

The bioactive material is coated onto the medical device, for example the stent 10 of FIG. 1, so as to be released from the medical device into the tissues of the vessel 24, and should be dispensed at a rate suitable for treating the required medical condition. In the case of a stent or other implantable medical device, it may be desirable for the bioactive material to be released over a prolonged period of time, for example weeks or months.

It is important that the bioactive agent is held onto the medical device during deployment of the device in the patient without excessive loss of bioactive material into the patient's bloodstream, for instance. For this purpose, the prior art has suggested restraining the bioactive material, for instance in a containment or time release layer or matrix. Examples include: porous polymer layers into which bioactive material can be embedded, enclosed chambers holding the bioactive material, outer coatings disposed over the bioactive material which dissolve or open during the deployment process, encapsulation of the bioactive material in capsules or pellets, and so on. Such containment measures can lead to a number of disadvantages, including undesirable delayed administration of the bioactive material into body tissues, presence of a foreign substance in the body, possible onset of stenosis caused by the carrier device, and the like.

It has been found that the optimal solution is to apply the bioactive agent in the absence of any containment or time release substance and from a layer which is predominantly or entirely made of bioactive agent(s). In this manner, after administration of the bioactive agent or agents, the medical device remains free of agent delivery substances (polymer layers, for example) and no unnecessary carrier substances are released into the patient's body. The problem, however, has existed with getting a bioactive agent to be held sufficiently well on the medical device.

The inventors have discovered that certain treatments of the medical device, and in particular of the surface or surfaces of the device intended to be coated with one or more bioactive agents, can substantially increase the adhesion of the bioactive agent to the device, before and during its deployment in a patient. Specifically, as described in the applicant's British patent application number 1600808.8 filed 15 Jan. 2016, the inventors have discovered that it is possible to increase substantially the adhesive qualities of a stent, by increasing the surface energy of those contact surfaces, and that this can avoid the need for any other mechanisms to retain the bioactive agent on the device. That patent application focuses specifically on functionalising the coated surfaces of the medical device by acidification or basification. They have also discovered, as demonstrated below, that this treatment or functionalisation can allow significantly more bioactive agent to be carried on the medical device.

The term functionalisation as used herein denotes the treatment of the or one or more surfaces of the medical device, in one example with an acid or base, to cause a change in the surface characteristics of the surface. The choice of acid or base functionalisation is dependent upon the nature of the bioactive material or materials which will coat the surface or surfaces. Specifically, functionalisation is by the conjugate of the nature of the bioactive material. For instance, for a bioactive material which is a base (or predominantly a base) the surface is functionalised by acidification. On the other hand, for a bioactive material which is acidic (or predominantly acidic) the surface is functionalised by basification. Functionalisation deposits onto the surface or surfaces acid or base species, which bind to the device surface and provide a bonding site for the base or acid conjugate of the bioactive material. In many cases, the acid or base species are deposited as individual molecules. They do not form a polymer matrix, for instance. Bonding of the bioactive agent is by means of covalent forces, in which the base/acid or acid/base combinations form a Lewis adduct. Bioactive material molecules which overlie those directly attached to their covalent species will bind to other bioactive material molecules by same species covalent bonds.

In practice, acid/base functionalisation leads to an increase in the polar acid or polar base component of the surface or surfaces, which leads to a significant increase in the quality of adhesion of bioactive agent to the contact surface of the medical device, and also to a substantial improvement in uniformity of coating across the contact surface(s) of the medical device.

The treatment or functionalisation process does not remove the oxide layer on the contact surface or surfaces. In the case of acidification or basification, the attached acidic or base components could be described as becoming part of the oxide layer. Leaving the oxide intact maintains the stability of the treated surfaces of the medical device while altering the bonding properties of the oxide layer.

As will be apparent from the examples below, significant improvement in bioactive material retention on the device is experienced by treatment or functionalisation alone. Better retention is achieved, though, by first cleaning the contact surface or surfaces of the medical device to remove impurities, generally acquired during and after the manufacturing process. This can substantially increase the amount of carbon functional groups on the contact surface(s) of the medical device, leading to an even more uniform coating of bioactive material across the contact surface(s) of the medical device.

Functionalisation by acidification may be carried out by a relatively strong acid, for instance having a pH of around 1.5, although tests have shown that a large range of acids in a large pH range can be effective also. Functionalisation by basification may be carried out with a base of pH of around 8 to 9, although is possible with a variety of bases in a large pH range.

The examples described below relate to functionalisation by acidification. Citric acid and citrate are used as example materials for this functionalisation. It is believed that citrate acts as an acid as a result of its amphoteric properties. Other suitable carboxylic acids include acetic acid, lactic acid, adipic acid, oxalic acid, formic acid, levulinic acid and the like. Tests have also been performed using ascorbic acid and found to be advantageous. The skilled person will recognise from the teachings herein that many other acids can be used to achieve the same effects. It will be apparent that conjugates and derivatives may be equally suitable for such purposes. As an example only, hydroxamic acid is a suitable derivate of carboxylic acid.

The specific embodiments described below are directed to a stent formed of nickel titanium alloy (for instance Nitinol) which is coated with paclitaxel, a preferred bioactive agent. The skilled person will appreciate that this is an example only and that the teachings herein are applicable to the other stent materials, including metals, metal alloys and also polymer based stents. Examples include stainless steel, cobalt chromium and so on. The teachings herein are also applicable to the treatment of polymer surfaces, for instance the outer surface or surfaces of a medical balloon.

Figure 3:
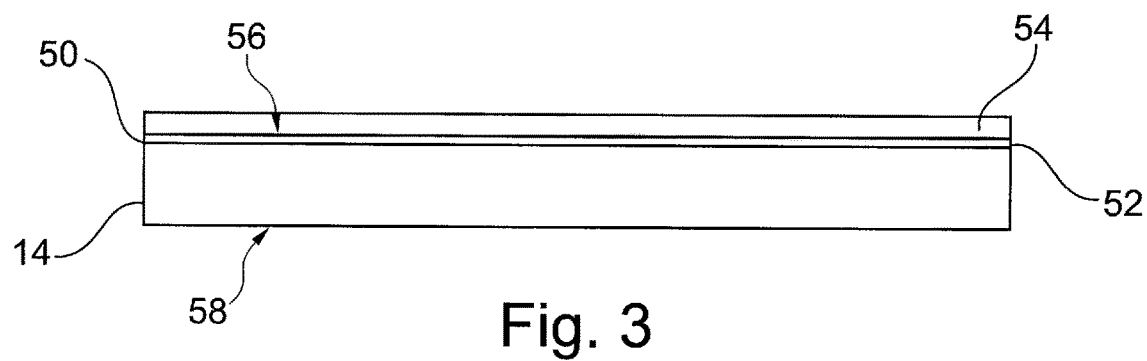
FIG. 3 is a schematic diagram of a transverse cross-sectional view of a stent strut of the stent of FIGS. 1 and 2 to show the functionalised contact surface and bioactive material coating.

Referring briefly to FIG. 3, this shows a schematic transverse cross-sectional view of a stent of the type shown in FIGS. 1 and 2. The tubular structure 12 of the stent, in particular strut 14, thereof has had its contact surface 50 functionalised by acidification or basification (with or without pre-cleaning) so as to have a functionalised contact surface 52 with the characteristics shown for example in FIGS. 4 and 5. Bioactive agent 54 is deposited onto the functionalised contact surface 52 (for example by spraying, rolling or dipping). It is not necessary to embed the bioactive agent in any containment matrix or layer, as is necessary with the prior art. It is preferred that the bioactive agent layer 54 is distinct from the base support (formed of the structure 14 and functionalised surface 52), that is sits on (above) the functionalised contact surface. The same applies to the embodiments which are treated other than by functionalisation. Thus, the exposed surface of the bioactive material layer 54 is solely the bioactive material (and possibly any functional groups includes with it, such as excipients and so on).

The stent 10 has at least one abluminal surface 56 and at least one luminal surface 58. The or each abluminal surface is on the tubular outer surface of the stent 10 (in this case the support structure) and will in practice face the vessel wall. On the other hand, the or each luminal surface 58 is on the tubular inner surface of the stent 10 and will in practice be exposed to blood flow. The teachings herein provide for forming the medical device, in this example the stent 10, to have different functional characteristics on its abluminal surfaces compared to its luminal surfaces. In particular, the abluminal surfaces are treated so as to have a high surface energy able to hold a bioactive agent such as a drug thereto without the need for a containment layer or material. On the other hand, the luminal surfaces are treated to as to have a low surface energy which avoids or reduces the chances of thrombosis caused by the presence of the medical device in the patient's vessel. As will be seen below, the preferred luminal treatment is to have a carbon layer on the oxide coating of the device structure, optionally formed thereon. Carbon can reduce surface energy and is biocompatible with a low thrombotic effect. A thicker carbon layer can lead to a lower surface energy.

In embodiments, as described in further detail below, the stent may be post processed by rolling, dipping or spraying in an acid, preferably citric acid, such that the abluminal surfaces of the stent (and the abluminal half of any lateral sides) are functionalised to a depth of around 100 nanometres with the luminal surfaces (and the luminal half of any lateral sides) kept free of such functionalisation.

Even though it has been found that functionalisation by acidification without any other surface treatment provides a notable increase in adhesion of a bioactive agent onto the medical device, it has been found that cleansing of the contact surface or surfaces of the medical device prior to acidification results in even better bioactive material retention on the medical device.

Cleaning with an alcohol, such as ethanol, can remove larger impurities from the contact surface. Plasma cleaning provides an atomically cleaned surface, removing in particular carbon components which may have adhered to the contact surface during or after manufacture. Any plasma treatment is chosen to be relatively low energy so as not to remove the oxide layer on the outer surface(s) of the medical device.

Suitable plasma machines include the Gatan Solarus Model 950 and Diener Femto type B. An example of an appropriate plasma cleaning treatment, for an $H_2 O_2$ plasma, has the following characteristics:

Vacuum=509-531 mTorr
Turbo Pump=750 Hz, 1.0 A
$H_2$ flow=6.3-6.4 sccm
$O_2$ flow=27.4-27.5 sccm
Power=50 W
Treatment time=5 minutes.

Plasma pre-treatment results in the generation of an even greater extent of functionalised polar species at the contact surface of the medical device during the process of acidification. The amount of titanium dioxide at the contact surface is substantially reduced compared to the case of functionalisation only. The predominant acidic species of the contact surface are, in this example: O—C=O, C—O, C—OH and C=O. These species provide an acid polar element to the surface energy of the contact surface(s) of the medical device and one which is very stable across the entire extent of the contact surface. As a result, even better retention of the bioactive agent to the contact surface is achieved.

The tubular structure 12 of the stent, in particular the struts 14 thereof, can be coated on their abluminal surfaces with a bioactive agent 54, deposited for example by spraying, rolling or dipping. It is not necessary to embed the bioactive agent in any containment matrix or layer, as is necessary with the prior art. It is preferred that the bioactive agent layer 54 is distinct from the base support (formed of the structure 14 and functionalised surface 52). Thus, the exposed surface of the bioactive material layer 54 is solely the bioactive material (and possibly any functional groups includes with it, such as excipients and so on).

The optional first cleaning stage cleans the stent 10 to remove large scale impurities and this may, as explained above, be by cleaning with ethanol or other suitable alcohol, or even water. In some embodiments, the entire stent can be electropolished.

Plasma provides atomic cleaning of the stent 10 and is most preferably by a low energy plasma. One example is an $O_2$ $H_2$ plasma which can remove impurities at the atomic level, whilst leaving the oxide layer on the base structure of the medical device intact. As explained above, other cleaning plasmas may be used, including for example of purified water and evaporated ethanol. Any other suitable atomic cleaning could be used in place of a plasma, for instance cleaning by $UV-O_3$, also known as UV Ozone.

Optional functionalisation of the contact surfaces of the stent 10 can be achieved by applying an acid or a base to the contact surfaces. This could be by dipping, rolling, spraying or any other suitable method. The acid or base may be at a concentration of around 1 g per 100 ml, although this depends on the nature of the acid/base used, the time of the functionalisation stage and so on. These are parameters which a person skilled in the art will be able to determine by experimentation.

The stent is advantageously allowed to dry prior to coating. Coating can be by spraying, dipping, rolling or any other suitable method, typically in a solution containing the bioactive agent. The coated stent is then dried.

The treatment, for instance functionalisation, of the surface of the stent 10 assists in attaching the bioactive agent to the stent 10. The higher surface energy of the stent leads to greater adhesive characteristics of the surfaces to be coated.

It is to be noted that following treatment or functionalisation, the surfaces of the medical device will have a very high surface energy. This very high surface energy can cause the medical device to be readily contaminated, for example if touched or placed within a dirty environment. As a result, it is important to handle the medical device very carefully after functionalisation, until the device is coated with the bioactive agent. This may be in a clean room environment, vacuum or the like. During this stage and in all subsequent stages until coating, the medical device is handled preferably without any contact made with the prepared surface(s) to be coated.

Figure 4:
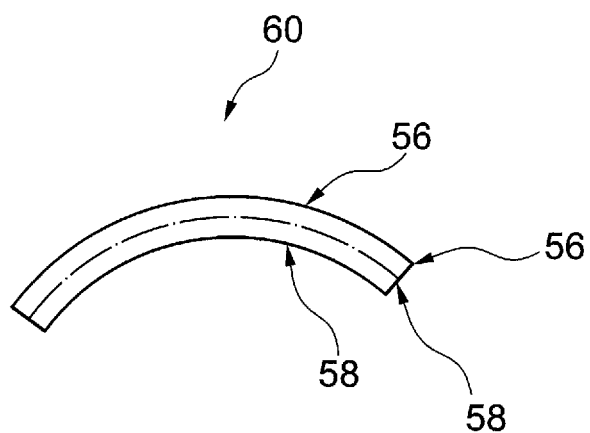
FIG. 4 is a schematic cross-sectional view of a stent strut to show the different surface treatments at the abluminal and the luminal sides of the stent and at the lateral walls thereof.

Referring now to FIG. 4 this depicts in schematic form a section of stent strut 60 taken transversely along the length of the stent 10 and showing the radial curvature of the stent strut 60 as would occur in practice. The abluminal side 56 of the strut 60, consistent with the abluminal side of the stent 10, is treated or functionalised to have a higher surface energy and may then be coated with a bioactive agent, typically a drug. In practice, both the abluminal surface of the stent and the lateral surfaces of the stent extending through the thickness of the stent, in the abluminal half of the side, are preferably treated to as to exhibit higher surface energy and to be coated with bioactive agent. By contrast, the luminal side 58 of the stent, and those portions of the side walls at the luminal side 58, are treated to have a lower surface energy and not be coated with a bioactive agent or drug. The lower surface energy of the luminal side and any luminal portions of the side walls reduces the risk of thrombus formation on the stent, as a low surface energy reduces the chance of foreign objects attaching to those stent surfaces. On the other hand, the high surface energy of the abluminal side and adjacent lateral wall portions are able to hold bioactive material thereto for treatment of the vessel wall.

Figure 5:
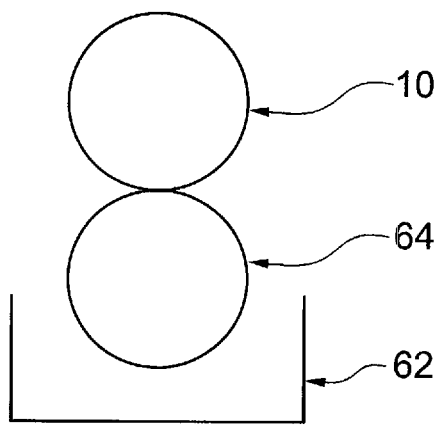
FIG. 5 is a schematic diagram of an embodiment of dipping process.

Referring now to FIG. 5, this shows in schematic form one example of apparatus for treating or coating the abluminal surfaces of a stent 10. In this embodiment, there is provided a chamber or bath 62 which may include cleaning fluid, functionalisation solution or bioactive agent solution, for application onto the abluminal surfaces of the stent 10. The apparatus also includes a transfer roller 64, which in practice will dip into the liquid in the bath 62 and the rotate so as to apply that liquid to the abluminal surfaces of the stent 10. It will be appreciated that the stent 10 may be held on a mandrel or other rotatable support, and that the stent 10 will rotate with the transfer roller 64 (in the opposite direction). In the simplest form, there would be a single motor driving the transfer roller 64.

This apparatus provides for simple selective treatment of the stent 10, and specifically of the abluminal surfaces thereof. The operation and effect of the apparatus shown in FIG. 4 will become apparent from the description of the treatment methods provided below.

Before discussing various stent treatment methods, reference is made to FIGS. 4 to 14 which show various embodiments of apparatus for performing these methods.

Figure 6:
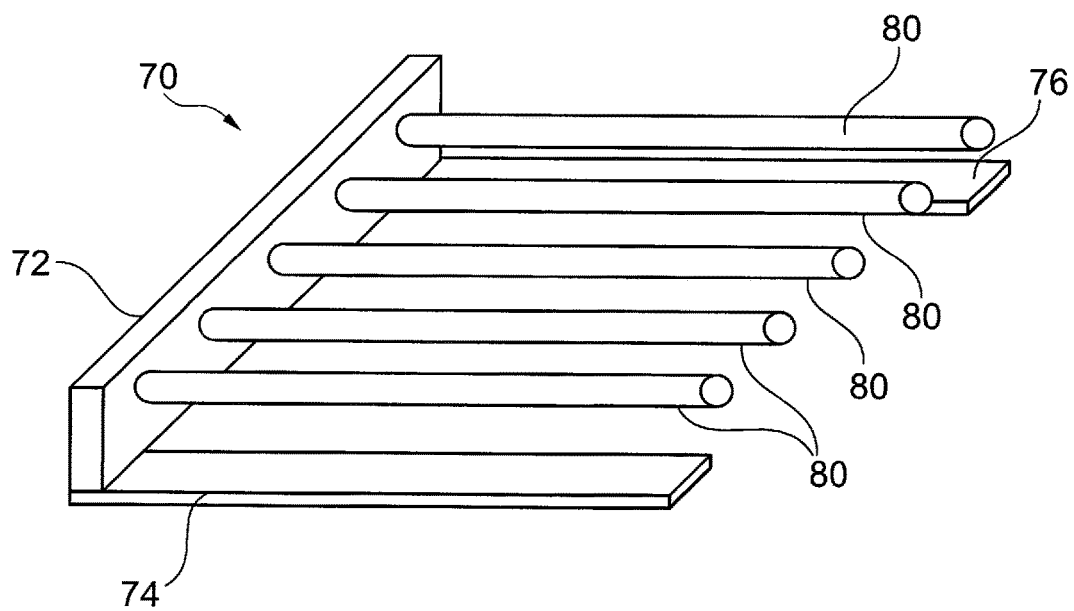
FIG. 6 is a schematic diagram of an embodiment of mandrel type plasma stent holder.
Figure 7:
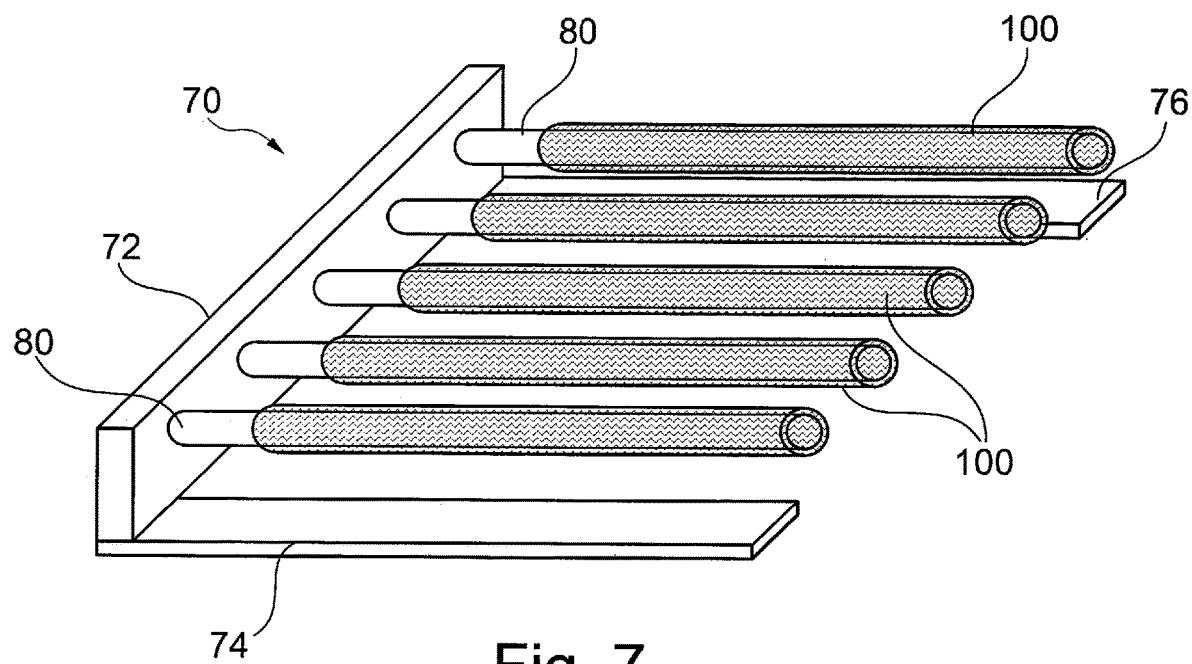
FIG. 7 is a schematic diagram of the stent holder of FIG. 6 with a series of stents held thereon.
Figure 8:
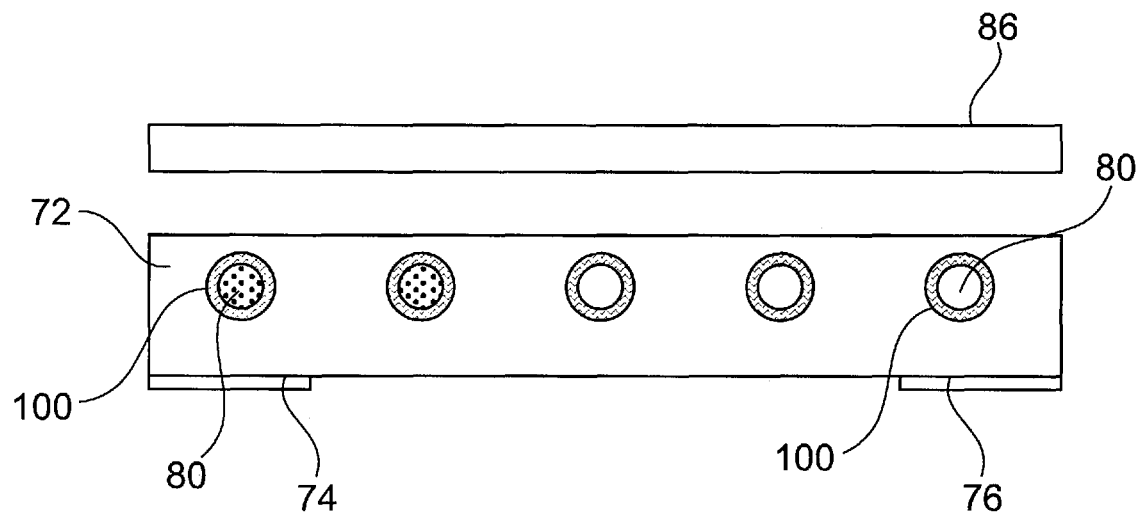
FIG. 8 is a front elevational view of the stent holder of FIGS. 6 and 7 under a plasma electrode.

Referring first to FIGS. 6, 7 and 8, these show a first embodiment of stent support frame 70 for holding a plurality of stents in order to treat the stents and then coat them with a bioactive material in accordance with the teachings herein. It will be appreciated that the frame 70 is only one component of the apparatus which will be used for treating and coating stents. As suitable apparatus is well known in the art, this is not described herein in detail nor shown in the drawings.

The frame 70 includes a support spine 72 of generally rectangular cubic form, which can be attached, in this example at its two ends, to legs 74, 76, which are also rectangular strips. The legs 74, 76 may be made of the same or a similar material as the support spine 72, for instance a metal, metal alloy, ceramic, plastics material or any other suitable material.

Extending from the support spine 72 is a series of mandrels 80, which extend in the same direction as the legs 74, 76 and have a length the same or similar to that of the legs 74, 76. The legs 74, 76 need only be long enough relative to the length of the mandrels 80 to support the mandrels when the structure 70 is a horizontal position, as shown in FIGS.

4, 5 and 6. In other words, the mandrels should remain suspended in a cantilevered fashion, both as shown in FIG. 4 and also when stents 100 are fitted thereto, as shown for example in FIGS. 5 and 6.

The mandrels 80 are each circular cylindrical rods or tubes. They may be immovably fixed to the support spine 72 but in some embodiments may be able to rotate about their axes relative to the support spine 72, in which case there may be provided either as an integral part of the support spine 72 or coupled thereto one or more motors for rotating the mandrels 80.

The mandrels 80 may be made of any suitable material and in the preferred embodiments of titanium, quartz or sapphire. Each mandrel 80 has a length suitable for accommodating stents to be treated and a diameter consistent with the inner diameter of when they are in their radially expanded condition, that is prior to radial crimping for fitting onto an introducer assembly. The stents are therefore treated and coated with bioactive material in the expanded condition. The skilled person will appreciate that the length and diameter of the mandrels 80 will vary in dependence upon the stents to be fitted thereto.

Referring to FIG. 8, this shows in schematic form the arrangement of the frame 70 and of the stents 100, when placed in a plasma chamber, with the plasma electrode 86 being depicted in schematic form and above the array of stents 100.

Examples of treatment methods which use the apparatus shown in FIGS. 6 to 8 are described below.

FIGS. 9 to 12 show another embodiment of support frame 90, which has a support spine 92 similar to the support spine 72 of the embodiments of 6 to 8 and first and second support legs 94, 96 equivalent to the support legs 74 and 76. The apparatus 90 differs by having a plurality of pairs of wire holders 90, which otherwise could be described as narrow diameter rods. These extend from the support spine 92 in the direction of the legs 94, 96, in similar manner to the mandrels 80 of the embodiment of FIGS. 6 to 8. The wires or rods 98 may be fixed in place or alternatively may be rotatable along their axes, by means of one or more motors integral with or attached to the support spine 92. As will be apparent in particular from FIGS. 9, 11 and 12, the wires or rods 98 are arranged in pairs spaced from one another in a pair by less than the diameter of a stent 100 intended to be supported by the wire/rod pair 98. As a result, a stent 100 can be placed on top of a pair of wires or rods 98.

Figure 12:
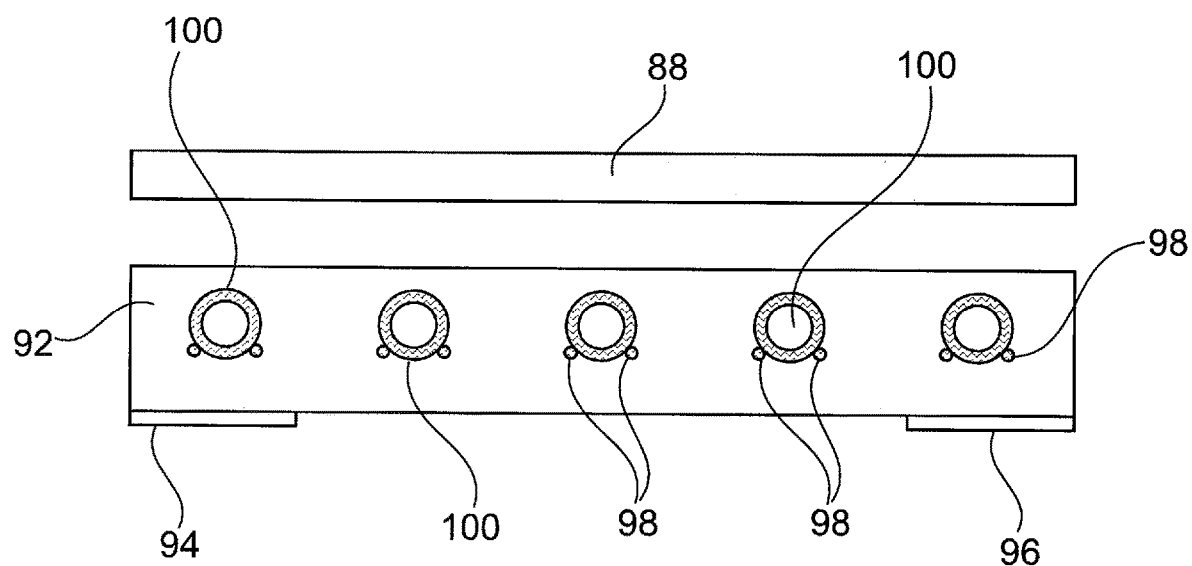
FIG. 12 is a front elevational view of the wire type stent holder of FIGS. 9 to 11 under a plasma electrode.

In FIG. 12 the frame 90 is depicted in a plasma chamber, with a plasma electrode 88 disposed above the stents 100.

Figure 13:
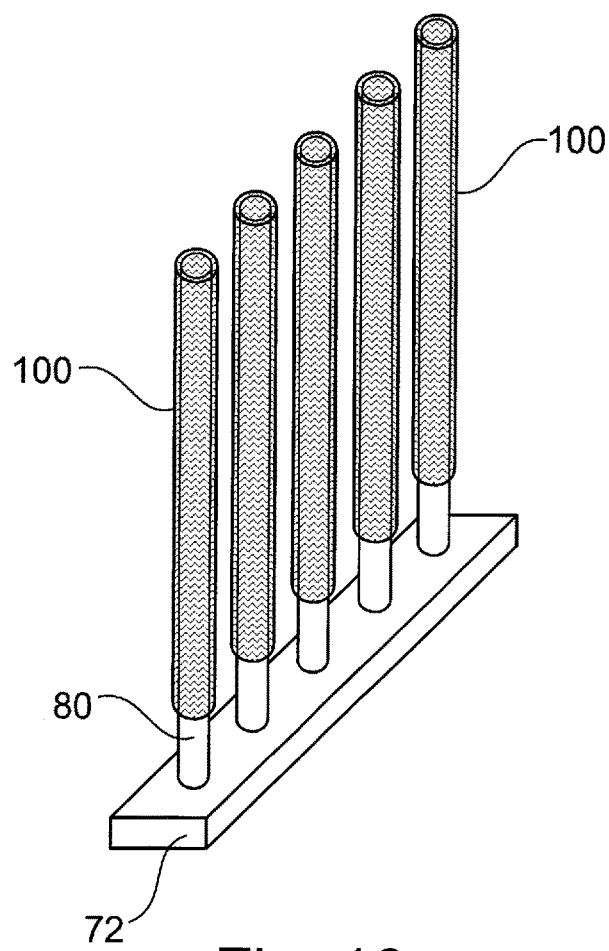
FIG. 13 is a schematic diagram of an embodiment of mandrel type spray stent holder.

Referring now to FIG. 13, this shows how a series of stents 100 can be disposed for treatment of its abluminal surfaces, particularly by a spray treatment. In this example, the stents may be carried on a support spine 72 to which are connected a series of mandrels 80, which may be fixed or rotatable in a similar manner to the apparatus shown in FIGS. 6 to 8, with stents 100 fitted onto respective mandrels 80. The arrangement shown in FIG. 13 is similar to that of FIGS. 6 to 8 save for the omission of the support legs 74, 76. In some embodiments, the apparatus shown in FIG. 13 may be the same as that shown in FIGS. 6 to 8, with the legs 74, 76 having been removed, and could be a leg-detachable version of the apparatus of FIGS. 6 to 8. The mode of usage of the apparatus shown in FIG. 13 is also described in further detail below.

Figure 14:
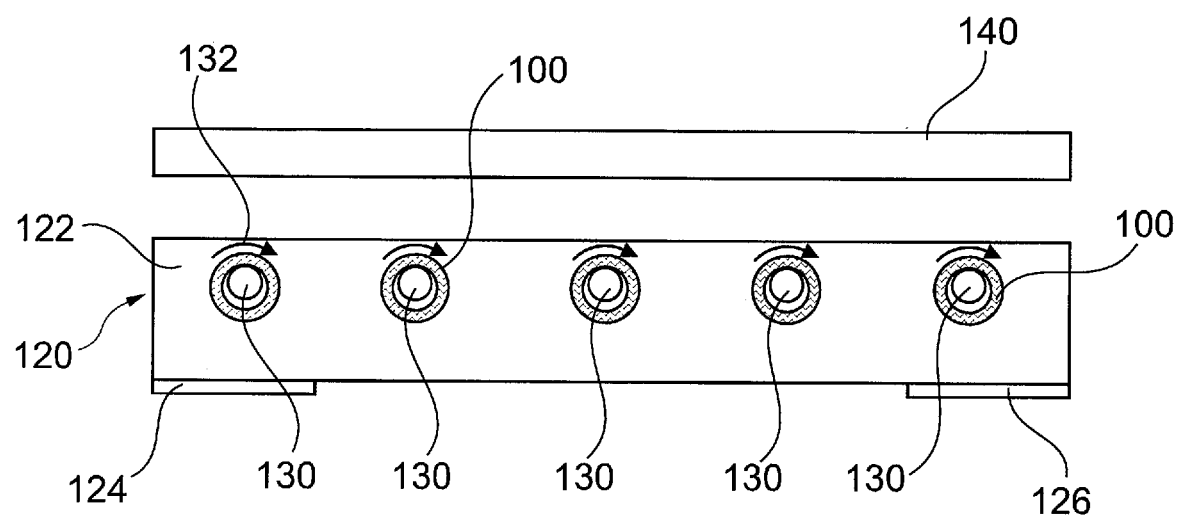
FIG. 14 is a schematic diagram of an embodiment of mandrel type UV Ozone stent holder.
Figure 15:
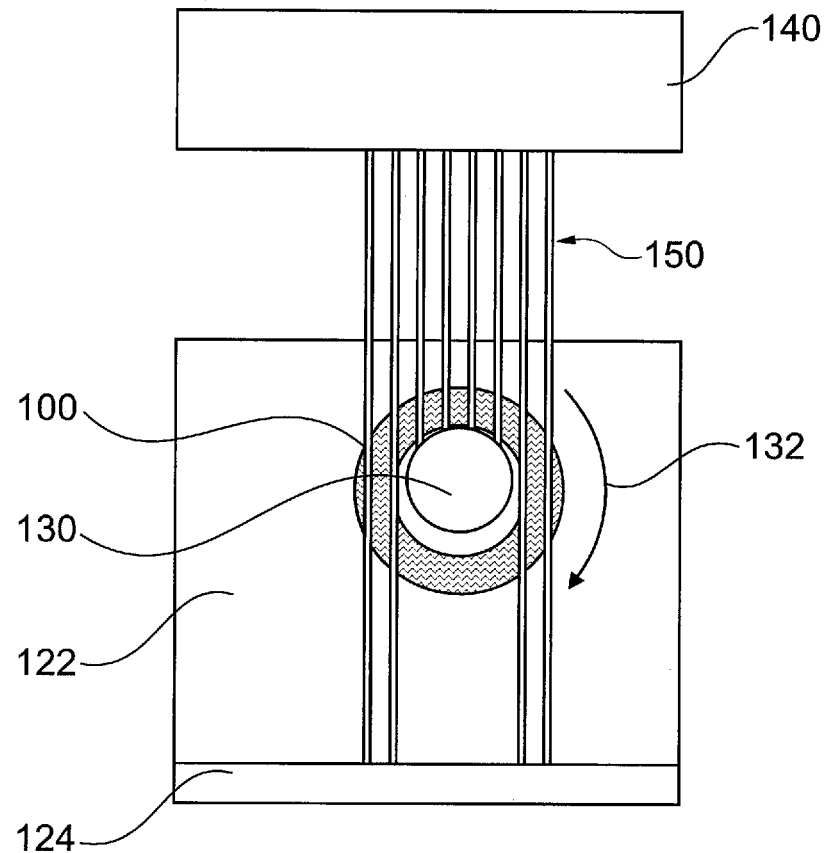
FIG. 15 is a schematic diagram of a part of the stent holder of FIG. 14.

With reference now to FIGS. 14 and 15, these show yet another embodiment of apparatus for surface treating of a stent and in particular the abluminal surfaces of the stent. The apparatus includes a frame 120 which includes a support spine 122 coupled to first and second legs 124, 126. The frame 120 is similar to the frames 70 and 90 shown in the embodiments described above. Extending from the support spine 122, in the same direction as the legs 124, 126, is a series of mandrels 130, which are coupled to one or more motors so as to be able to rotate in the direction of the arrows 132. As with the previously described embodiments; the mandrels 130 may be driven by a common motor or by individual motors, and are preferably rotated at the same time and at the same rate, so that the stents go through the same treatment process at the same rate and at the same time. FIG. 15 is an enlarged view of a part of the apparatus of FIG. 14 and shows at reference numeral 150 the direct line of sight of the cleaning effect provided by an UV Ozone plasma. In this embodiment it is therefore not necessary for the mandrels 130 to be in tight contact with the inner, luminal, surfaces of the stents 100 to prevent treatment of the luminal surfaces of the stent, since the UV Ozone plasma only cleans in the direction of the "line of sight".

With regard to the various examples of apparatus described above and shown in FIGS. 6 to 15 in particular, there follows a description of various different embodiments of methods for obtaining a high surface free energy on the abluminal surfaces of a medical device, in this example a stent, while leaving the luminal surfaces unaffected, that having a low surface free energy. It will be appreciated that the methods described below are alternatives to the transfer roller method which would be operated by means of the apparatus shown schematically in FIG. 5.

Method 1

After the entire stent 100 is washed in alcohol, such as ethanol, the stents 100 are fitted to their respective mandrels 80, as shown in FIGS. 6 and 7. Each stent 100 fits tightly onto its associated mandrel 80, so as to seal the luminal surfaces of the stent 100 against the mandrel.

The frame 70 is then placed into a plasma chamber, for example of the type described above, such that only the abluminal surfaces of the stent are cleaned in order to remove the carbon deposits from the abluminal surfaces of the stent. As described above, the plasma is preferably such as not to remove the oxide layer of the stent. The oxide layer can improve the biocompatibility of the stent and it is therefore considered advantageous that it remain intact. The plasma cleaning by this method will significantly increase the surface free energy of the abluminal surface(s) of the stent, which will increase ability to attach thereto bioactive agents such as any of the drugs disclosed herein.

It will be appreciated that prior to deposition of a bioactive agent, the stent is dried.

In this embodiment, no further treatment of the abluminal surface of the stent is contemplated, beyond coating with a bioactive agent. It will be appreciated, therefore, the bioactive agent will be attached directly to the plasma cleaned abluminal surface(s) of the stent.

Method 2

Similar to Method 1, the stents, after being washed in ethanol to remove volatile components, are placed on their respective mandrels 80, as shown in FIGS. 6 and 7, with the luminal surfaces of the stent being contacted by (sealed to) the mandrel so as not to be subjected to any further treatment. The stents 100 are then plasma cleaned, in the same way as Method 1 above. Following plasma cleaning, in this embodiment, the abluminal surfaces of the stent are functionalised by acid vapour deposition within the plasma chamber, by means of any of the acids disclosed herein, preferably citric acid. As a result, the abluminal surfaces of the stent 100 are both plasma cleaned and functionalised by acidification. The acid may be applied by a solution, with the solvent being dried. The stent is dried prior to deposition of a bioactive agent.

Method 3

Similar to Method 1, the stents 100 are first cleaned in ethanol (or other alcohol) in order to remove volatile components. The stents 100 are then placed onto their respective mandrels 80, as per FIGS. 6 and 7, with the luminal surfaces being sealed to the mandrel, prior to plasma cleaning in a plasma chamber as per FIG. 8. After plasma cleaning, the abluminal surfaces of the stent may be functionalised by acid treatment, by dipping or preferably by spraying. For this purpose, the support spine 72 is preferably removable from the apparatus, with the mandrels 80 attached thereto, that is in the form shown in FIG. 13, such that the stents 100 remain on their respective mandrels 80 and can be handled without direct touching. These are then dipped into acid bath or sprayed with an acid to functionalise the surfaces. As the luminal surfaces of the stents are protected by the mandrels 80, these are not affected by the plasma treatment or the acidification.

Method 4

Figure 9:
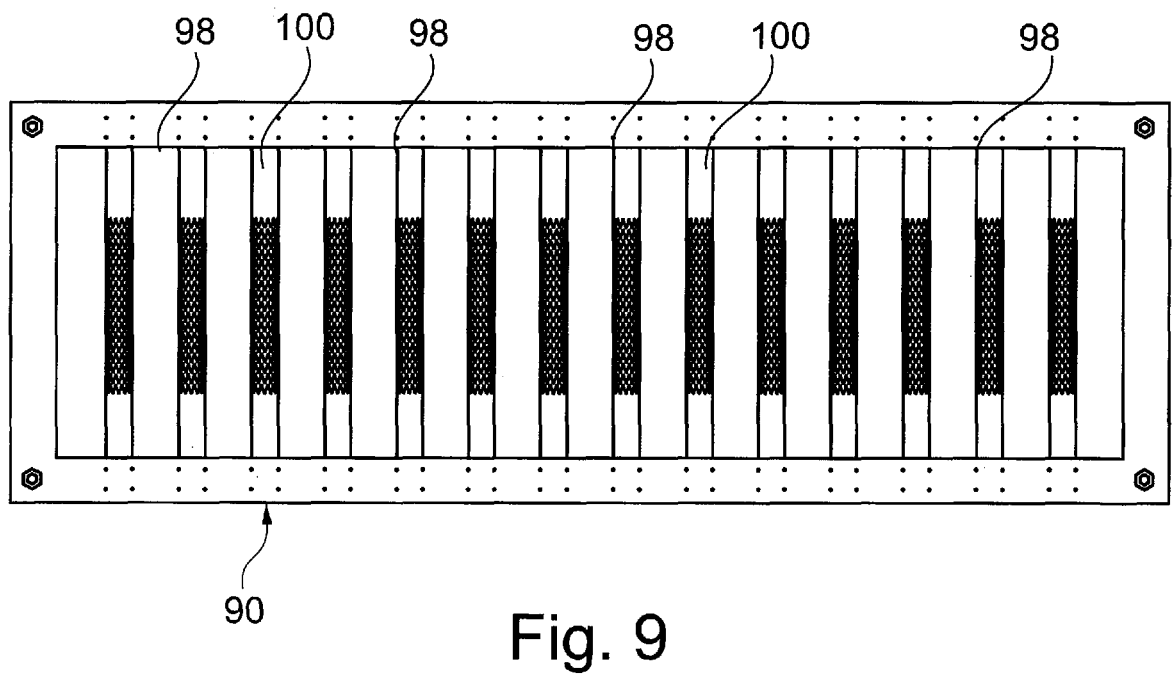
FIG. 9 is a photograph of an embodiment of wire type plasma stent holder.
Figure 10:
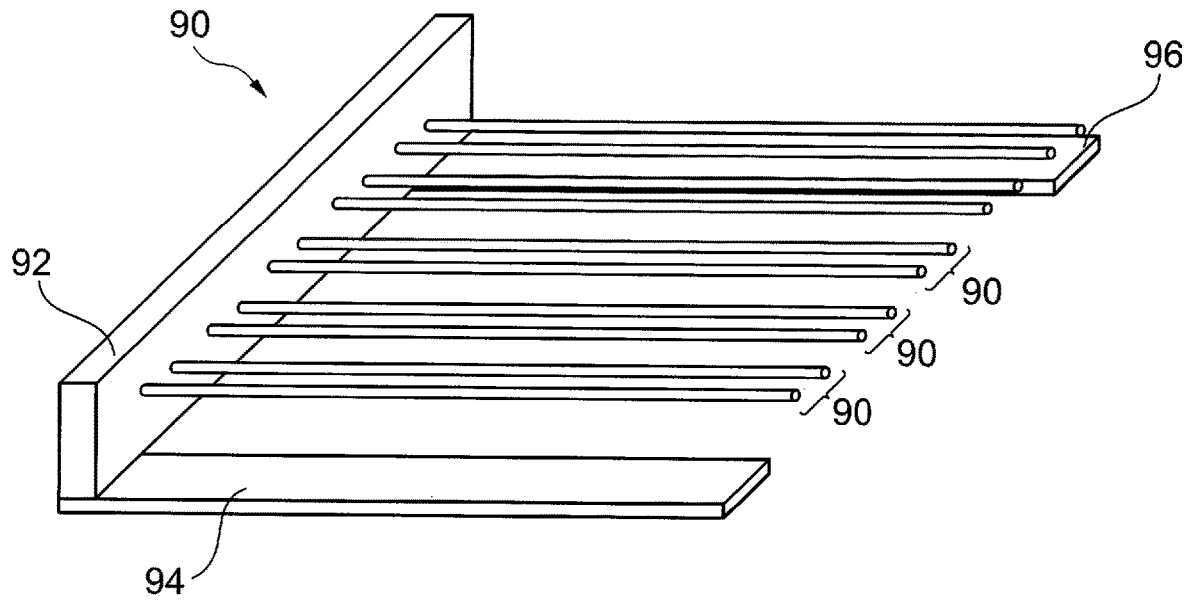
FIG. 10 is a schematic diagram of the wire type plasma stent holder of FIG. 8 with a frame element of the holder removed.
Figure 11:
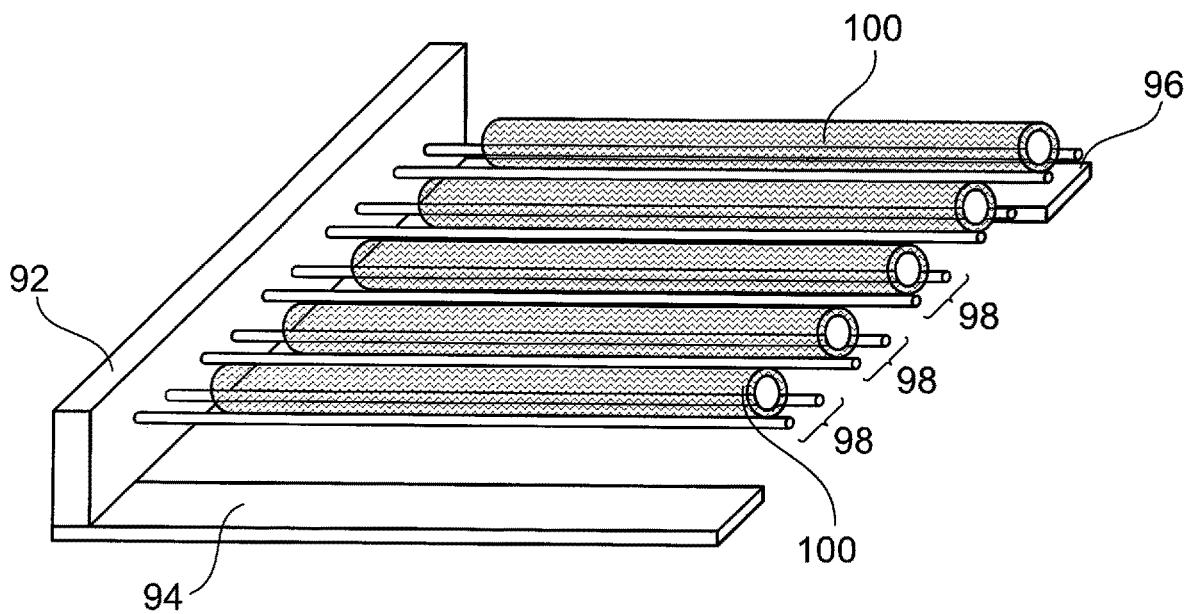
FIG. 11 is a schematic diagram of the wire type plasma stent holder of FIGS. 9 and 10 with stents disposed thereon.

With reference now to FIGS. 9 to 12, after the volatile components are removed from the stent surfaces, by ethanol washing for example, the stents are placed on the frame 90, as shown in particular in FIGS. 9 and 11. The holder 90 can be placed into a plasma tube, as depicted in FIG. 12, for plasma cleaning as described above. In this arrangement, all of the surfaces of the stents 100, that is the abluminal as well as the luminal surfaces (and the lateral sides) are plasma cleaned, which will remove the carbon deposits from the entirety of exposed surfaces of the stent 100. It will be appreciated that by rotation of the wires or rods 98 even those parts the stents 100 which are initially in contact with the wires 98 will become exposed to the plasma cleaning.

This cleaning process will remove all carbon components from the stent, so this method redeposits carbon on all of the surfaces, again using a suitable plasma. Examples include IPA or an ethanol plasma. Once carbon has been redeposited, the stents are further treated in a frame 70 of the type shown in FIGS. 6 to 8, by means of any of the methods 1, 2 or 3 described above.

Method 5

The stents are first cleaned to remove volatile components, by alcohol, preferably ethanol, cleaning and then placed on a holder of the type shown in FIG. 13, with the luminal surfaces of stents 100 sealed to the mandrels 80, in the manner explained above. The stents 100 are then treated by spraying the abluminal surfaces of the stent with an acid so as to functionalise these surfaces. The luminal surfaces are not exposed to the acid treatment. The stents can then be further treated by coating the abluminal surfaces with a bioactive agent as taught herein. It will be appreciated that in this method the stents are not plasma cleaned.

Method 6

This method uses the apparatus depicted in FIGS. 14 and 15.

As with the previous methods, the stents are treated to remove volatile components, by alcohol, preferably ethanol, washing and the stents then placed on the frame 120 in the manner shown in FIGS. 14 and 15. The abluminal surfaces of the stents 100 are then cleaned by US Ozone treatment, with the advantage of UV Ozone over plasma being that the UV Ozone is a direct line of sight cleaning system, as depicted in FIG. 15. In this example, therefore, the stents 100 can be placed loosely on the mandrels 130, as opposed to having to be fitted tightly to the mandrels 80 in methods 1 to 3. This makes it easier for the stents 100 to be loaded and unloaded onto the frames, compared to the arrangement in FIGS. 6 to 8, the latter being necessary since plasma will circulate all around the stent, making it necessary to seal the luminal surfaces.

The abluminal surfaces of the medical device are preferably impervious, that is the bioactive agent does not and cannot seep into the medical device so as to be held therewithin, but instead remains as a distinct layer on top of the abluminal surfaces. Similarly, the carbon coating on the luminal surfaces of the medical device are also impervious, which reduces the risk of thrombi being formed by the device when implanted in a patient.

It is contemplated that in some embodiments one side of the stent, typically the luminal side, is coated with carbon in dispersive form whereas the other surface or surfaces of the stent, typically on the abluminal side, are coated with polar carbon.

In some embodiments, it is not necessary to take any action to have a carbon coating on the luminal surface since it will naturally have a carbon coating. In some embodiments, carbon deposits can be applied by exposing the luminal surface to air.

The carbon coating is advantageously amorphous carbon, that is not crystalline such as diamond-like carbon. The carbon may be present as a free element and/or chemically linked with oxygen and/or hydrogen, for example.

The bioactive agent, or material, can be any of a large range of suitable agent variety and many are known in the art. The layer of bioactive agent applied to the functionalised surfaces of the device may be of a single bioactive material or a combination of different bioactive agents, in dependence upon the desired treatment. There may also be provided other active agents in the bioactive material layer, such as excipients or other release facilitators.

The bioactive material is preferably paclitaxel but may include any one or more of: paclitaxel and/or paclitaxel derivatives, rapamycin and/or rapamycin derivatives, docetaxel and/or docetaxel derivatives, cabazitaxel and/or cabazitaxel derivatives, taxane and/or taxane derivatives, estrogen or estrogen derivatives; heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopdine or another antiplatelet agent; colchicine or another antimitotic, or another microtubule inhibitor; cytochalasin or another actin inhibitor; a remodelling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anti-cancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; 60Co (having a half-life of 5.3 years), 192Ir (73.8 days), 32P (14.3 days), 111In (68 hours), 90Y (64 hours), 99mTc (6 hours) or another radio therapeutic agent; iodine containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alphatocopherol, superoxide dismutase, deferoxyamine, a 21-aminosteroid (lasaroid) or another free radical scavenger, iron chelator or antioxidant; angiopeptin; a 14C-, 3H-, 131I1-, 32P- or 36S-radiolabelled form or other radio labelled form of any of the foregoing; or a mixture of any of these.

Examples of suitable excipient include: urea and/or urea derivatives, gallates and gallate derivatives (such as epi gallo catechin gallate), saccharides and/or saccharide derivatives, chitin and/or chitin derivatives, ascorbic acid, citric acid, sterates and/or sterate derivatives, polyvinyl pyrolidone, dicalcium phosphate dihydrate, eudragit polymers and/or eudragit polymers derivatives, cellulose and/or cellulose derivatives, PEG, poylsorbate 80, sodium lauryl sulphate, chitosan, magnesium dioxide, silicon dioxide, carbonate derivatives, plasdone, butylated hydroxyanisole, succinic acid, sodium dioctyl sulfosuccinate, precirol ATO 5 or tannic acid may be added to the bioactive agent. An excipient will speed up the release of the bioactive agent once the medical device is deployed within the patient, for instance by the excipient dissolving within the patient's blood plasma and providing for quick release of the bioactive agent. This can be particularly useful in treating initial reactive hyperplasia occurring as a result of angioplasty, stent implantation or other medical procedures. Where an excipient is used, this may be as a sublayer between the layer of bioactive material and the medical device or as a layer above the layer of bioactive material. The excipient acts to speed the release of the bioactive agent (drug for example), compared to a drug per se or a drug held in a containment or time release layer. In the case of a sublayer of excipient, the functionalisation of the surface to be coated will be matched to the nature of the excipient and the excipient matched to the bioactive agent or agents.

The teachings herein make it possible to attach bioactive agents to the surfaces of medical devices without having to rely on binding agents or polymer of other matrix materials as in the prior art. Binding agents are considered to be substances which enhance the adhesion of a bioactive material layer at the support surface and generally act to retard the release of the bioactive agent or agents. A polymer or other matrix performs a similar role. Binding agents and matrices act as containment mechanisms.

At the same time, while optimising the adherence qualities of the abluminal surface(s) of the medical device, its luminal surface(s) are made relatively less active by having significantly lower surface energy.

As described above, although bioactive agents or materials are used in many embodiments, the bioactive agent or material is therapeutic and in some embodiments a therapeutic agent or material may be used which is not necessarily bioactive. Examples of therapeutic agents or material are provided below.

The therapeutic substance could be used for inhibiting the activity of vascular smooth muscle cells. More specifically the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of embodiments of this present invention. For example, the agent can be for enhancing wound healing in a vascular site or improving the structural and elastic properties of the vascular site. Examples of agents include anti-proliferative substances such as actinomycin D, or derivatives and analogues thereof.

Synonyms of actinomycin D include dactiomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifebrin, antithrombin, antimitotic, antibiotic, antiallergeric and antioxidant substances. Examples of such antineoplastics and/or antimitotics include paclitaxel, docetaxel methotrexate, azathioprine, vincristine, vinblastine, fluorouracil, doxorubicin hydrochloride and mitomycin. Examples of such antiplatelets, anticoagulants, antifibrin, and anthithrombins include sodium heparin, low molecular weight heparins, heparinoids, hirudin, argatroban, forskolin, vapiprost, prostacyclin and prostacyclin analogues, dextran, D-phe-pro-arg-chloromethlyketone (synthetic antithrombin), dipyridamole, glycoprotein IIb/IIIA platelet membrane receptor antagonist antibody, recombinant hirudin, and thrombin inhibitors such as Angiomax. Examples of such cytostatic or antiproliferative agents include angioprotein, angiotensin converting enzyme inhibitors such as captopril, cilazapril or Lisinopril; calcium channel blockers (such as nifedipine), colchicine, fibroblast growth factor antagonists, fish oil, histamine antagonists, lovastatin, monoclonal antibodies, nitroprusside, suramin, serotonin blockers, steroids, thioprotease inhibitors, triazolopyrimidine, and nitric oxide. An example of an antiallergic agent is permirolast. Other therapeutic substances or agents which may be appropriate include alpha-interferon, genetically engineered epithelial cells, rapamycin and dexamethasone.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in British patent application number 1702525.5, from which this application claims priority, and in the abstract accompanying this application, are incorporated herein by reference.

What is claimed is:

1. An implantable medical device including a support structure having at least one abluminal surface having a first surface energy, at least one luminal surface having a second surface energy, and a therapeutic material disposed on the at least one abluminal surface;
   wherein the second surface energy is less than the first surface energy;
   wherein the at least one luminal surface includes a coating of or comprising carbon,
   wherein the coating of carbon on the at least one luminal surface is an innermost surface of the medical device
   wherein the at least one luminal surface of the support structure includes an oxide layer, the coating of carbon being disposed over of the oxide layer;
   wherein the support structure is a stent,
   wherein the at least one abluminal surface is on a tubular outer surface of the stent, and
   wherein the at least one luminal surface is on a tubular inner surface of the stent.

2. An implantable medical device according to claim 1, wherein the at least one abluminal surface is a functionalised surface.

3. An implantable medical device according to claim 1, wherein the abluminal surface is free of polymer and matrix materials.

4. An implantable medical device according to claim 1, wherein the abluminal surface is free of containment and time release elements.

5. An implantable medical device according to claim 1, including a therapeutic material coating disposed directly on the at least one abluminal surface so as to overlie the at least one abluminal surface, the therapeutic material coating attaching to the at least one abluminal surface as a result of the first surface energy thereof.

6. An implantable medical device according to claim 1, wherein the abluminal surface is functionalised by at least one polar acid or by at least one polar base component, so as to be a functionalised surface.

7. An implantable medical device according to claim 6, including a therapeutic material coating disposed directly on the at least one abluminal surface so as to overlie the at least one abluminal surface, the coating being a conjugate base or including a conjugate base component of the polar acid or being a conjugate acid or including a conjugate acid component of the polar base.

8. An implantable medical device according to claim 7, wherein the therapeutic material coating disposed directly on the at least one abluminal surface so as to overlie the at least one abluminal surface is free of containment or time release materials.

9. An implantable medical device according to claim 1, wherein the therapeutic material is a bioactive material.

10. A method of preparing an implantable medical device according to claim 1, including the steps of:

treating the at least one abluminal surface of the stent to increase the surface energy of the at least one abluminal surface relative to the at least one abluminal surface, said treatment step not being carried out on the at least one luminal surface.

11. A method according to claim 10, including the steps of subjecting the at least one abluminal surface to a treatment or functionalisation agent while keeping the at least one luminal surface apart from the treatment or functionalisation agent.

12. A method according to claim 10, wherein the at least one luminal surface is covered during treatment or functionalisation of the at least one abluminal surface.

13. A method according to claim 10, wherein the at least one abluminal surface is passed through a bath of functionalising solution while the at least one luminal surface is kept remote from the functionalising solution.

14. A method according to claim 10, including the step of washing the entire support structure in an alcohol, sealing the at least one luminal surface and plasma cleaning the at least one abluminal surface.

15. A method according to claim 14, wherein the alcohol is ethanol.

16. A method according to claim 10, wherein at least the abluminal surface or surfaces are plasma cleaned.

17. A method according to claim 10, wherein both the abluminal and luminal surfaces are plasma cleaned.

18. A method according to claim 10, wherein at least the abluminal surface or surfaces are cleaned by UV Ozone.

* * * * *